May 31, 1949. J. D. BROWNELL Plant Pat. 842
ROSE PLANT
Filed April 22, 1946
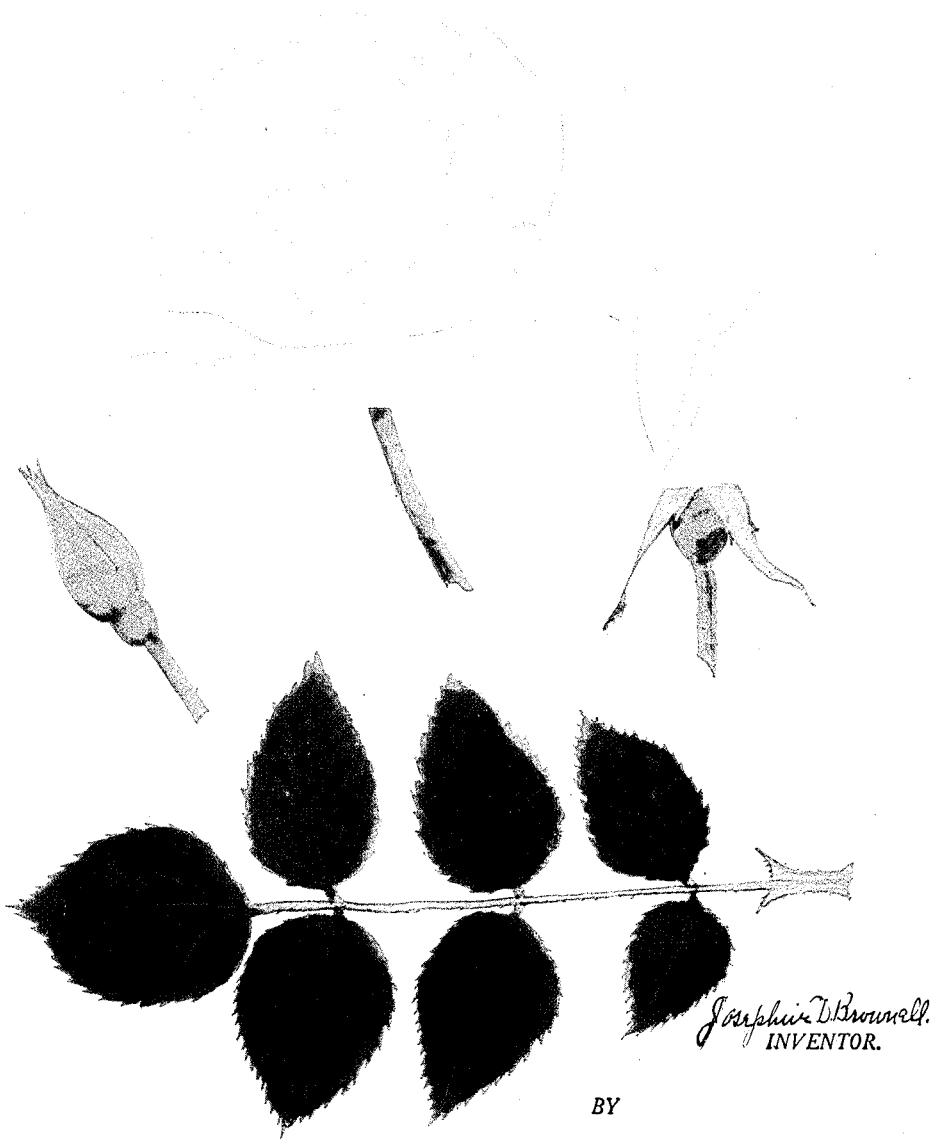

Patented May 31, 1949

Plant Pat. 842

UNITED STATES PATENT OFFICE

842

ROSE PLANT

Josephine D. Brownell, Little Compton, R. I.

Application April 22, 1946, Serial No. 663,869

1 Claim. (Cl. 47—61)

My invention relates to rose plants and especially to a new, original and distinct variety of the class known commercially as "hybrid teas" and is a variant in that class, being a *Rosa wichuraiana* hybrid tea, produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana,* of hardiness, or immunity from serious injury on account of cold temperatures prevailing in certain parts of the northern United States, and of special vigor, bloom quantity and foliage resistance.

The red to pink shades (ordinary dictionary definition) of the inner side of its petals and the red to pink shades on the outer side, in combination with the unique brilliance thereof and their tendency to hold these colors under exposure;

The novelty and variation within certain definite limits of the form of the bloom, its character of holding that form for a long time, and the petallage of the flowers;

Its character of tightly recurling outward of its petals;

Its character of fragrance;

Its unusual abundance of flowers;

The intensity of its remontant and overblooming or reblooming character;

Its character of ascending in height by recurrent branching and progressively longer stems from the base in some instances long enough to to be classified as canes;

The character of producing many seven leafleted leaves which character seldom has obtained on hybrid teas not having *Rosa wichuraiana* ancestry, but frequently obtains on flower stems of descendants of *Rosa wichuraiana* of the dwarf reblooming type.

And especially its characteristic of partial freedom from premature defoliation by black-spot, under certain definite conditions of exposure, without any cultural control.

In the accompanying drawing forming a part of this specification I have shown my new rose in its natural colors, that is as near as is possible to do so artificially.

My new rose is otherwise described as follows:

*Essential information*

*Type.*—Hybrid tea, *Rosa wichuraiana* hybrid, dwarf to ascending to tall to climber, for garden display, cut flower and forcing or growing under glass.

*Class.*—Hybrid tea crossed with *Rosa wichuraiana,* further restricted by originator to include only those varieties that can survive moderately low sub-zero temperatures.

*Breeding.*—This variety was produced and bred by me and under my direction by cross pollenation.

It came into being as a seedling grown from a seed borne on a plant, of the variety "Pink Princess," Plant Patent Number 459 and the pollen parent of my new rose was "Crimson Glory," Plant Patent Number 105.

The pollenation that fertilized the seed that grew into this new rose, as well as the pollenation that produced one of its parents were directed by me and were performed by emasculating flowers and placing thereon a bag protecting them from self and foreign pollen. These bags were later removed and the flowers were hand pollenated with a camel's hair brush and the bags immediately replaced. The date of this pollenation was July 1, 1943.[1] The seed was planted under my direction on December 8, 1943, and the date of the first flower was July 14, 1944.

The plant and flower seemed to be of unusual merit and I have since made and directed extensive propagations and tests thereof.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August, in 1944–45 inclusive and the characters have successively reproduced, true to the original seedling.

*Flower*

*Habit.*—It blooms out of doors in Little Compton, beginning about three days prior to the average beginning time of commercial hybrid teas and continues relative to growth of the plant until frost.

*Flowers borne.*—Often one and frequently two or three and occasionally more on each stem, in the usual hybrid tea type of cluster. The pedicels and peduncles are medium in diameter and length, erect, stiff, almost smooth, free from large prickles and bristles but with several very small prickles varying to small rigid hairs of the same color as the prickles lower down on the stem.

[1] This and other dates herein are approximate.

Stems are long, diameter medium to slightly slender and notably stiff and rigid.

*Fragrance.* — Medium, distinctive, pleasing China tea in combination with that of *Rosa wichuraiana* under favorable environment, especially notable in warm, dry weather.

*Bud.*—Neck normal as described, opens well, being little to not at all affected by hot or wet weather or both, as to color and form, except at very high temperatures the color is less intense and the form of the petals is then only slightly less recurled.

Before the calyx breaks the size is medium, form notably pointed, frequently with one or more sepals having foliaceous parts extending beyond the apex of the calyx up to about one half of an inch, the number and size of the foliaceous parts being variable and frequently having one narrow, pointed, serrate appendage on one side of some of the sepals and frequently on both sides, otherwise the sepals are usually normal and regular, tapering to lanceolate at their apex, turning back nearly perpendicular to the pedicel to curved slightly downward as the bud opens.

Color of the bud as the calyx opens "Rose Red"[2] shading to "Rose Color" on the recurled edges as the petals begin to open.

*Bloom.*—As the flower opens and develops to maturity, the recurled edges turn to "Deep Rose Pink," and the balance of the petal colors vary from Deep Rose Pink to Rose Color and Rose Red. Just before the petals fall the color is in part "Amaranth Pink." The petals have a characteristic brilliance.

The flower is usually 3½ to 5 inches in diameter when fully open, infrequently more or less, petals vary from 40 to 60, frequently some smaller petals and petaloids in the center, variable in number.

The flower opens high centered, formal, tightly recurled, outward showing stamens and pistils in its last stages. The petals are variable from obovate to ovate to irregular and frequently with surfaces of petaloids variously warped and edges especially of the smaller petals frequently irregular. The larger petals often have one or two small notches, one each side of short apex that varies irregularly from slightly acute. Texture is medium to thick and leathery; both sides satiny; with slight veining which is not prominent. The time of opening in favorable conditions is four to five days.

The petals are substantial and after about five to six days drop off cleanly, except that occasionally one or two inner petals or petaloids cling to turn dull, to fall later. The flower does not "ball" in wet weather. The flower lasts well, is only slightly affected at any stage by moderate cold or hot temperatures, or by humidity or wet weather.

*Reproductive organs.*—Stamens, quantity variable, around medium or slightly uneven lengths; usually more than 75.

Anthers, Light Salmon Orange.

Filaments, nearly Mustard Yellow.

Pistils are several of slightly uneven lengths, averaging about one-half inch long.

Ovaries are usually all inclosed.

Hips frequently develop to ovoid to globular, color comparable with under side of leaves with variable colored overlay on the side exposed to the sun, moderately smooth; walls, thin, fleshy.

Sepals are persistent and break off easily.

Seeds variable in number.

[2] This and other color names hereinafter are from Robert Ridgway "Color Standards."

*Plant*

*Foliage.*—Is abundant, of compound leaves of three to five leaflets near the flower, five leaflets lower down the stem and frequently seven leaflets nearer the base. Size of leaflets medium to small, averaging on young plants in size a little larger than half way between the average hybrid tea and the *Rosa wichuraiana* leaflets. As the plants develop in size some of the leaflets develop to twice the size described above. Form of leaflets usually ovate with apex slightly acute, base rounded. Edges very slightly warped with serrations nearly regular and medium to fine in size.

The color of the upper surface when the stem is in flower is Dark Dull Yellow Green to Dark Green, under side Bice Green to Light Bice Green.

The petioles are medium with several minute hairs on the upper sides or edges and small prickles on the under sides, nearly straight, all substantially the same color as the leaves, the prickles often tinged with Dahlia Carmine and the upper surface of petioles often show slightly overlay of Dahlia Carmine, more pronounced toward the base.

The stipules are medium long from about one-half to three quarters of an inch long, medium width about one quarter inch wide, with pointed apexes the inner sides of which form an angle of about 90°. The edges have many very short minute hairs.

Stems are medium to large as the plant develops, color Bice Green, side toward sun frequently shaded with Dahlia Carmine, the pedicels notably so. The prickles are nearly Dahlia Carmine, turning to more colorless, usually two to four between leaves.

*Growth.*—Habit is hybrid tea type of growth, to ascending by branching and growth from the base.

*Winter resistance.*—From tests at Little Compton, Rhode Island, this new rose plant compares in winter resistance with that of the sub-zero hybrid tea, "Pink Princess."

*Comparisons.*—The nearest rose of hybrid tea type is its seed parent Pink Princess which opens less recurled. The color and color pattern is different in that the color of this new rose is more nearly Rose Red to Rose Color. And the new rose can bear more flowers more constantly, under favorable conditions.

In comparison with Plant Patent 459 the bloom normally opens in a more nearly spherical form; the recurl in hot weather is more intense and constant; it recurls more tightly, the diameter of the recurl being normally about one half that of Plant Patent 459, and usually about twice as many recurls to the recurl area.

The blooms of my new rose on well established plants frequently obtain clusters of normally large flowers on longer stems as many as three times in number; blooms more and more constantly;

The color is notably darker averaging under certain environmental conditions approximately twice as dark; the branching habit includes normally the growth at mid season of a stem or cane of growth in length and thickness notably exceeding any such under the more gradual stem development of Plant Patent 459; on stems that develop three blooms, the peduncles frequently branch from the stem notably closer together;

The angle at which the stems seek to grow forms a somewhat wider angle in relation to the gravitational influence; it does not set hips as freely.

My new rose has bloomed more and more constantly at Little Compton, Rhode Island, than any other garden rose of a definite hybrid tea type, known to me.

In comparison with the variety of the application 663,871; the bloom frequently has approximately twice as many petals that are in nearly all instances under nearly all environmental conditions notably more recurled, open in a more compact and formal manner; emit a fragrance more nearly of the China tea rose character and notably less of the carnation fragrance; the angle at which the stems seek to grow in relation to the gravitational influence is greater; the branching habit includes normally the growth at mid season of a stem or cane of growth in length and thickness notably exceeding any such under the more gradual stem development of Plant Patent 459; on stems that develop three blooms the peduncles frequently branch from the stem notably closer together; the stems average in diameter about 50% greater; it blooms more and more constantly.

I claim:

The hardy hybrid *Rosa wichuraiana* hybrid tea, rose plant variety substantially as herein disclosed, characterized by its resistance to winter injury, its mild pleasing fragrance, with leaflets of a brilliant green with form and color of bloom and plant substantially as described and shown, and with petals that recurl outward in a unique degree of tightness and form, of unique form of growth and very great degree of inflorescence and continuity thereof.

JOSEPHINE D. BROWNELL.

REFERENCES CITED

The following references are of record in the file of this patent:

UNITED STATES PATENTS

| Number | Name | Date |
|---|---|---|
| Pl. Pt. 459 | Brownell | Mar. 4, 1941 |